(12) United States Patent
Takamoto

(10) Patent No.: US 11,810,373 B2
(45) Date of Patent: Nov. 7, 2023

(54) COGNITIVE FUNCTION ESTIMATION DEVICE, LEARNING DEVICE, AND COGNITIVE FUNCTION ESTIMATION METHOD

(71) Applicant: Mitsubishi Electric Corporation, Tokyo (JP)

(72) Inventor: Shusaku Takamoto, Tokyo (JP)

(73) Assignee: Mitsubishi Electric Corporation, Tokyo (JP)

( * ) Notice: Subject to any disclaimer, the term of this patent is extended or adjusted under 35 U.S.C. 154(b) by 0 days.

(21) Appl. No.: 17/637,310

(22) PCT Filed: Sep. 19, 2019

(86) PCT No.: PCT/JP2019/036686
§ 371 (c)(1),
(2) Date: Feb. 22, 2022

(87) PCT Pub. No.: WO2021/053780
PCT Pub. Date: Mar. 25, 2021

(65) Prior Publication Data
US 2022/0277570 A1    Sep. 1, 2022

(51) Int. Cl.
*G06V 20/59* (2022.01)
*G06V 10/80* (2022.01)
(Continued)

(52) U.S. Cl.
CPC ............ *G06V 20/597* (2022.01); *A61B 5/162* (2013.01); *A61B 5/18* (2013.01); *G06V 10/40* (2022.01);
(Continued)

(58) Field of Classification Search
CPC .... G06V 20/597; G06V 10/40; G06V 10/806; G06V 20/56; G06V 40/168; A61B 5/162;
(Continued)

(56) References Cited

U.S. PATENT DOCUMENTS 9,707,971 B2 * 7/2017 Takahashi .............. B60K 35/00
11,544,937 B2 * 1/2023 Minami ................. G06V 20/58
(Continued)

FOREIGN PATENT DOCUMENTS

CN    105809152 A    7/2016
CN    110211401 A    9/2019
(Continued)

OTHER PUBLICATIONS

Office Action dated Nov. 28, 2022 from the German Patent Office in Application No. 112019007558.6.
(Continued)

*Primary Examiner* — Md K Talukder
(74) *Attorney, Agent, or Firm* — Sughrue Mion, PLLC; Richard C. Turner

(57) ABSTRACT

Provided are a vehicle outside information acquiring unit to acquire vehicle outside information, a face information acquiring unit to acquire face information, a biological information acquiring unit to acquire biological information, a vehicle information acquiring unit to acquire vehicle information, a vehicle outside information feature amount extracting unit to extract a vehicle outside information feature amount on the basis of the vehicle outside information, a face information feature amount extracting unit to extract a face information feature amount in accordance with the vehicle outside information feature amount, a biological information feature amount extracting unit to extract a biological information feature amount in accordance with the vehicle outside information feature amount, a vehicle information feature amount extracting unit to extract a vehicle information feature amount in accordance with the vehicle outside information feature amount, and a cognitive function estimation unit to estimate whether a cognitive function of a driver is low on the basis of a machine learning
(Continued)

model, the vehicle outside information feature amount, and at least one of the face information feature amount, the biological information feature amount, or the vehicle information feature amount.

10 Claims, 4 Drawing Sheets

(51) Int. Cl.
    *G06V 40/16* (2022.01)
    *G06V 10/40* (2022.01)
    *G06V 20/56* (2022.01)
    *A61B 5/16* (2006.01)
    *A61B 5/18* (2006.01)

(52) U.S. Cl.
    CPC ............ *G06V 10/806* (2022.01); *G06V 20/56* (2022.01); *G06V 40/168* (2022.01)

(58) Field of Classification Search
    CPC ..... A61B 5/18; A61B 5/7264; A61B 2503/22; G08B 21/02
    See application file for complete search history.

(56) References Cited

U.S. PATENT DOCUMENTS

| | | | |
|---|---|---|---|
| 2018/0220948 A1* | 8/2018 | Kojima | A61B 5/7246 |
| 2019/0092337 A1 | 3/2019 | Chua et al. | |
| 2019/0167175 A1* | 6/2019 | Kojima | A61B 5/024 |
| 2019/0265699 A1 | 8/2019 | Yabuuchi et al. | |
| 2019/0370580 A1* | 12/2019 | Aoi | G06V 10/454 |
| 2020/0031365 A1* | 1/2020 | Marti | B60K 35/00 |
| 2022/0277570 A1* | 9/2022 | Takamoto | G06V 40/168 |

FOREIGN PATENT DOCUMENTS

| | | |
|---|---|---|
| DE | 112017007267 T5 | 11/2019 |
| JP | 2015-080549 A | 4/2015 |
| JP | 2018-050847 A | 4/2018 |
| JP | 2017-37306 A * | 9/2018 |
| JP | 2018-142259 A | 9/2018 |
| JP | 2018-151902 A | 9/2018 |
| JP | 2018-190140 A | 11/2018 |
| WO | 2018/158622 A1 | 9/2018 |
| WO | 2018/158704 A1 | 9/2018 |
| WO | 2018/203470 A1 | 11/2018 |

OTHER PUBLICATIONS

International Search Report for PCT/JP2019/036686 dated Nov. 26, 2019 [PCT/ISA/210].

Written Opinion for PCT/JP2019/036686 dated Nov. 26, 2019 [PCT/ISA/237].

Japanese Office Action for Japanese Patent Application No. 2021-546128 dated Oct. 26, 2021.

Chinese Office Action dated Jun. 29, 2023 in Chinese Application No. 201980100335.1.

* cited by examiner

FIG. 2

| Vehicle Outside Information Feature Amount | Face Information Feature Amount | Biological Information Feature Amount | Vehicle Information Feature Amount |
|---|---|---|---|
| Red Traffic Signal Information | Line-of-Sight Direction, Face Direction | — | Brake Operation Information, Reaction Time Until Brake Operation, Accelerator Operation Information |
| Green Traffic Signal Information | Line-of-Sight Direction, Face Direction | — | Accelerator Operation Information, Reaction Time Until Accelerator Operation |
| Running out Information | Eye-opening Degree, Face Direction, Line-of-Sight Direction, Emotion Information | Pulse, Heart Rate | Brake Operation Information, Reaction Time Until Brake Operation, Steering Wheel Operation Information, Reaction Time Until Steering Wheel Operation |
| Traffic Sign Information of Temporary Stop | Line-of-Sight Direction, Face Direction | — | Brake Operation Information |
| Information Indicating Traveling on Same Road | Emotion Information | Pulse, Heart Rate | Navigation Device Operation Information, Position Information |
| ... | ... | ... | ... |

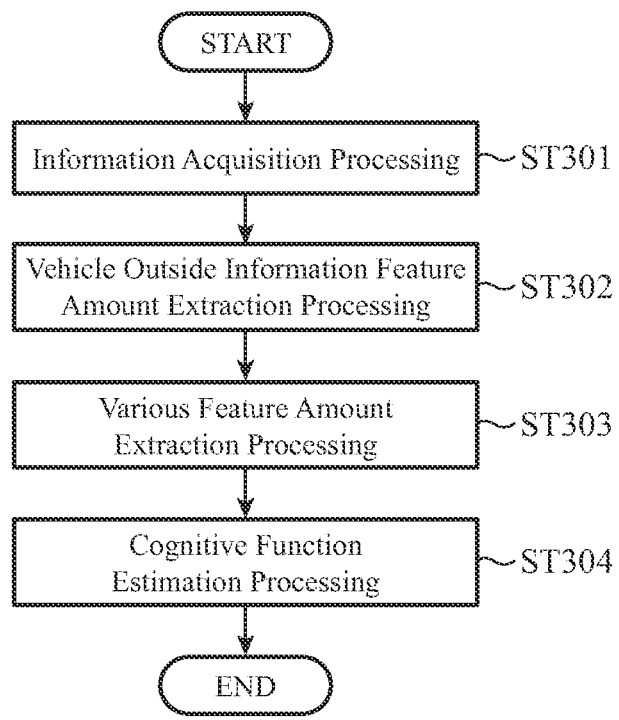
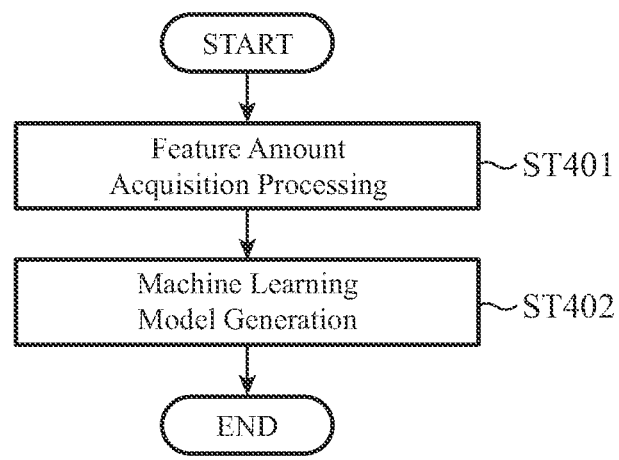

COGNITIVE FUNCTION ESTIMATION DEVICE, LEARNING DEVICE, AND COGNITIVE FUNCTION ESTIMATION METHOD

CROSS REFERENCE TO RELATED APPLICATIONS

This application is a National Stage of International Application No. PCT/JP2019/036686 filed Sep. 19, 2019.

TECHNICAL FIELD

The present invention relates to a cognitive function estimation device that estimates a cognitive function of a driver of a vehicle, a learning device that learns the cognitive function of the driver of the vehicle, and a cognitive function estimation method that estimates the cognitive function of the driver of the vehicle.

BACKGROUND ART

In general, it is known that the cognitive function of a person decreases as the person ages. The cognitive function mentioned here is a function of a person for appropriately driving a vehicle. For example, when the driver of a vehicle is elderly, the cognitive function is deteriorated, so that the driver may not be able to perform the cognitive function, and as a result, the driver may not be able to appropriately drive. Therefore, for example, in a driving assistance technique, a technique for estimating whether or not a driver has a certain level of cognitive function is required.

On the other hand, as a technology related to the degree of cognition of a driver in the sense of the degree of concentration on driving, for example, Patent Literature 1 discloses a cognition degree estimation device that estimates the degree of cognition on the basis of movement in the vertical direction of the line of sight of the driver of a vehicle.

CITATION LIST

Patent Literatures

Patent Literature 1: JP 2015-80549 A

SUMMARY OF INVENTION

Technical Problem

As described above, the driving assistance technique requires a technique for estimating whether or not the driver has a certain level of cognitive function. However, the conventional driving assistance technique has a problem that the cognitive function of the driver cannot be estimated.

The cognition degree estimation device as disclosed in Patent Literature 1 estimates the degree of cognition, but the degree of cognition is a temporary degree of concentration on driving of a driver. Thus, the device does not estimate whether or not the driver has a certain level of function for appropriately driving a vehicle. Therefore, the technology of the cognition degree estimation device as disclosed in Patent Literature 1 cannot solve the above problem.

The present invention has been made to solve the above problem, and an object of the present invention is to provide a cognitive function estimation device capable of estimating whether or not a driver has a certain level of cognitive function.

Solution to Problem

A cognitive function estimation device according to the present invention includes: processing circuitry to acquire vehicle outside information on a situation around a vehicle; to acquire face information on a face of a driver of the vehicle; to acquire biological information of the driver; to acquire vehicle information on the vehicle; to extract a vehicle outside information feature amount for estimation of a cognitive function of the driver on the basis of the vehicle outside information acquired to extract, in accordance with the vehicle outside information feature amount extracted, a face information feature amount for the estimation of the cognitive function of the driver on the basis of the face information acquired to extract, in accordance with the vehicle outside information feature amount extracted, a biological information feature amount for the estimation of the cognitive function of the driver on the basis of the biological information acquired; to extract, in accordance with the vehicle outside information feature amount extracted, a vehicle information feature amount for the estimation of the cognitive function of the driver on the basis of the vehicle information acquired; and to estimate whether or not the cognitive function of the driver is low on the basis of a machine learning model, the vehicle outside information feature amount extracted, and at least one of the face information feature amount extracted, the biological information feature amount extracted, or the vehicle information feature amount extracted.

Advantageous Effects of Invention

According to the present invention, it is possible to estimate whether or not the driver has a certain level of cognitive function.

BRIEF DESCRIPTION OF DRAWINGS

FIG. 2 is a diagram for explaining a concept of an example of a relationship between a vehicle outside information feature amount extracted by a vehicle outside information feature amount extracting unit and a face information feature amount extracted by a face information feature amount extracting unit, a biological information feature amount extracted by a biological information feature amount extracting unit, or a vehicle information feature amount extracted by a vehicle information feature amount extracting unit in the first embodiment.

FIG. 3 is a flowchart for explaining an operation of the cognitive function estimation device according to the first embodiment.

FIG. 4 is a flowchart for explaining an operation of a learning device according to the first embodiment.

DESCRIPTION OF EMBODIMENTS

Hereinafter, an embodiment of the present invention will be described in detail with reference to the drawings.

First Embodiment

Figure 1:
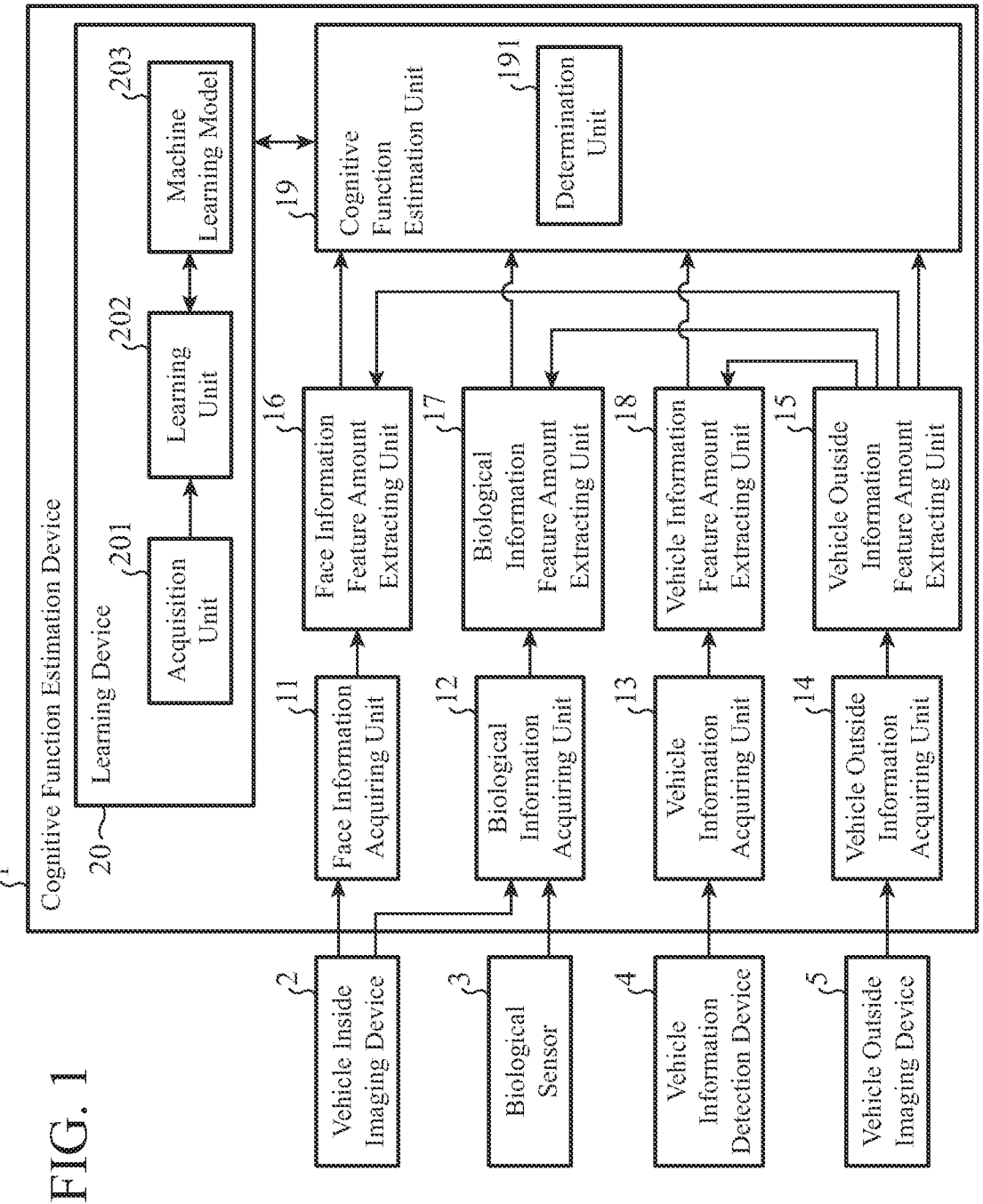
FIG. 1 is a diagram illustrating a configuration example of a cognitive function estimation device according to a first embodiment.

FIG. 1 is a diagram illustrating a configuration example of a cognitive function estimation device 1 according to a first embodiment.

The cognitive function estimation device 1 according to the first embodiment is assumed to be mounted on a vehicle (not illustrated).

As illustrated in FIG. 1, the cognitive function estimation device 1 is connected to a vehicle inside imaging device 2, a biological sensor 3, a vehicle information detection device 4, and a vehicle outside imaging device 5. The vehicle inside imaging device 2, the biological sensor 3, the vehicle information detection device 4, and the vehicle outside imaging device 5 are assumed to be mounted on the vehicle.

The vehicle inside imaging device 2 images the inside of the vehicle. The vehicle inside imaging device 2 is, for example, a vehicle inside camera or the like installed in the vehicle for the purpose of monitoring the inside of the vehicle, and is installed in such a way as to be able to image an area in the vehicle including at least an area in which the face of the driver seated on the driver's seat should be present. The area in which the face of the driver seated on the driver's seat should be present is, for example, an area corresponding to a space near the front of the headrest of the driver's seat. The vehicle inside imaging device 2 may be an imaging device included in a so-called "driver monitoring system" mounted on the vehicle for monitoring a state of the driver in the vehicle.

The biological sensor 3 measures biological information of the driver. The biological information of the driver is, for example, information on pulse, body temperature, blood pressure, respiration, heart rate, or brain waves of the driver.

The vehicle information detection device 4 detects vehicle information on the vehicle. The vehicle information detection device 4 includes various devices that detect information on the vehicle, such as an accelerator opening degree sensor, a steering angle sensor, a brake sensor, a global positioning system (GPS), and a navigation device. The vehicle information is, for example, information on an accelerator opening degree, information on a steering wheel steering angle, or information on a brake operation amount. For example, when the vehicle information detection device 4 is an accelerator opening degree sensor, the accelerator opening degree sensor detects that the accelerator is operated, the accelerator opening degree of the vehicle, or the like. Further, for example, when the vehicle information detection device 4 is a steering angle sensor, the steering angle sensor detects a steering wheel steering angle or the like of the vehicle. Further, for example, when the vehicle information detection device 4 is a brake sensor, the brake sensor detects that a brake of the vehicle is operated, a brake operation amount, or the like. Further, for example, when the vehicle information detection device 4 is the GPS, the GPS detects the current position of the vehicle. Furthermore, for example, when the vehicle information detection device 4 is a navigation device, the navigation device detects that the navigation device is operated, route information of the vehicle, or the like.

The vehicle outside imaging device 5 is, for example, a vehicle outside camera that images an area around the vehicle.

The cognitive function estimation device 1 estimates the cognitive function of the driver of the vehicle on the basis of a machine learning model 203, an image captured by the vehicle outside imaging device 5 (hereinafter, referred to as a "vehicle outside captured image"), and at least one of an image captured by the vehicle inside imaging device 2 (hereinafter, referred to as "vehicle inside captured image"), biological information measured by the biological sensor 3, or vehicle information measured by the vehicle information detection device 4. Here, the "model" is a learned model in machine learning. The machine learning model 203 is generated by a learning device 20 using machine learning. Details of the learning device 20 and the machine learning model 203 will be described later.

In the first embodiment, the "cognitive function" refers to a function of a person for appropriately driving a vehicle. When the driver has a certain level of cognitive function, the driver can appropriately drive the vehicle. On the other hand, when the cognitive function of the driver is deteriorated, the driver cannot appropriately drive the vehicle, for example, by performing a certain violation in driving the vehicle. Generally, it is said that the cognitive function is deteriorated as the age increases.

The cognitive function estimation device 1 includes a face information acquiring unit 11, a biological information acquiring unit 12, a vehicle information acquiring unit 13, a vehicle outside information acquiring unit 14, a vehicle outside information feature amount extracting unit 15, a face information feature amount extracting unit 16, a biological information feature amount extracting unit 17, a vehicle information feature amount extracting unit 18, a cognitive function estimation unit 19, and the learning device 20.

The cognitive function estimation unit 19 includes a determination unit 191.

The learning device 20 includes an acquisition unit 201, a learning unit 202, and the machine learning model 203.

The face information acquiring unit 11 acquires a vehicle inside captured image from the vehicle inside imaging device 2, and acquires face information on the face of the driver of the vehicle on the basis of the vehicle inside captured image. In the first embodiment, the face information of the driver is information on the face direction of the driver, information on the line of sight of the driver, information on the eye-opening degree of the driver, information on the mouth-opening degree of the driver, emotion information based on the expression of the driver, information on the position of the head of the driver, or the like. For example, the face information acquiring unit 11 may acquire the face information of the driver from the vehicle inside captured image using a known image recognition technology.

The face information acquiring unit 11 outputs the acquired face information to the face information feature amount extracting unit 16. The face information acquiring unit 11 may accumulate the acquired face information in a storage unit (not illustrated).

The biological information acquiring unit 12 acquires biological information of the driver of the vehicle from the biological sensor 3.

The biological information acquiring unit 12 may acquire a vehicle inside captured image from the vehicle inside imaging device 2 and acquire biological information from the vehicle inside captured image using an existing image recognition technology. Specifically, for example, the biological information acquiring unit 12 analyzes a luminance change of the driver's face in the vehicle inside captured image using an existing image recognition technology. Then, the biological information acquiring unit 12 estimates, for example, the pulse of the driver from the analyzed luminance change of the driver's face.

The biological information acquiring unit 12 outputs the acquired biological information to the biological information feature amount extracting unit 17. The biological information acquiring unit 12 may accumulate the acquired biological information in the storage unit.

The vehicle information acquiring unit 13 acquires vehicle information on the vehicle from the vehicle information detection device 4.

The vehicle information acquiring unit 13 outputs the acquired vehicle information to the vehicle information feature amount extracting unit 18. The vehicle information acquiring unit 13 may accumulate the acquired vehicle information in the storage unit.

The vehicle outside information acquiring unit 14 acquires a vehicle outside captured image from the vehicle outside imaging device 5, and acquires vehicle outside information on the situation around the vehicle on the basis of the vehicle outside captured image. In the first embodiment, the vehicle outside information is information on a traffic signal, information on whether or not a pedestrian runs out, information on a route on which the vehicle is traveling, information on a traffic sign, or the like. The information on a traffic signal includes, for example, information on the presence or absence of a traffic signal and the color of a traffic signal. The information on a traffic sign includes, for example, information on the presence or absence of a traffic sign and the content of a traffic sign. The vehicle outside information acquiring unit 14 may acquire the vehicle outside information from the vehicle outside captured image using, for example, a known image recognition technology. Furthermore, the vehicle outside information acquiring unit 14 may use the vehicle outside captured image itself acquired from the vehicle outside imaging device 5 as the vehicle outside information.

The vehicle outside information acquiring unit 14 outputs the acquired vehicle outside information to the vehicle outside information feature amount extracting unit 15. The vehicle outside information acquiring unit 14 may accumulate the acquired vehicle outside information in the storage unit.

The vehicle outside information feature amount extracting unit 15 extracts a vehicle outside information feature amount for estimation of the cognitive function of the driver on the basis of the vehicle outside information acquired by the vehicle outside information acquiring unit 14.

As a specific example, for example, in a case where information on a traffic signal is included in the vehicle outside information and the traffic signal is a red traffic signal, the vehicle outside information feature amount extracting unit 15 extracts information indicating the red traffic signal as a vehicle outside information feature amount for estimation of the cognitive function of the driver. At this time, the vehicle outside information feature amount extracting unit 15 can also include, for example, information indicating the position of the traffic signal in the real space in the vehicle outside information feature amount. It is assumed that an imaging area of the vehicle outside captured image is determined in advance, and the vehicle outside information feature amount extracting unit 15 may calculate the position of the traffic signal in the real space on the basis of, for example, the vehicle outside captured image, map information, and position information of the vehicle. For example, the vehicle outside information feature amount extracting unit 15 may acquire the map information from a navigation device (not illustrated) mounted on the vehicle. In addition, the vehicle outside information feature amount extracting unit 15 may acquire the position information of the vehicle from the GPS. Note that the position of the traffic signal in the real space may be calculated by the vehicle outside information acquiring unit 14 and output to the vehicle outside information feature amount extracting unit 15 as the vehicle outside information.

In addition, for example, in a case where information on a traffic signal is included in the vehicle outside information and the traffic signal is a green traffic signal, the vehicle outside information feature amount extracting unit 15 extracts information indicating the green traffic signal as a vehicle outside information feature amount for estimation of the cognitive function of the driver. At this time, the vehicle outside information feature amount extracting unit 15 can also include, for example, information indicating the position of the traffic signal in the real space in the vehicle outside information feature amount.

Furthermore, for example, in a case where a vehicle outside captured image is acquired as the vehicle outside information, when it is detected that a person has run out on the vehicle outside captured image, the vehicle outside information feature amount extracting unit 15 extracts information indicating that the person has run out as a vehicle outside information feature amount for estimation of the cognitive function of the driver. Note that, in this case, the vehicle outside information is, for example, a vehicle outside captured image, and the vehicle outside information feature amount extracting unit 15 may compare a vehicle outside captured image most recently accumulated in the storage unit with a vehicle outside captured image output from the vehicle outside information acquiring unit 14, and thereby detect whether or not a person has run out.

Furthermore, for example, in a case where the information on a traffic sign prohibiting vehicle entry is acquired as the vehicle outside information, the vehicle outside information feature amount extracting unit 15 extracts information indicating that there is the information on the traffic sign prohibiting vehicle entry as the vehicle outside information feature amount for estimation of the cognitive function of the driver. Furthermore, for example, in a case where information on a traffic sign for a temporary stop is acquired as the vehicle outside information, the vehicle outside information feature amount extracting unit 15 extracts information indicating that there is the information on the traffic sign for a temporary stop as a vehicle outside information feature amount for estimation of the cognitive function of the driver.

Furthermore, for example, in a case where similar vehicle outside information is repeatedly output within a preset period, the vehicle outside information feature amount extracting unit 15 extracts information indicating that the vehicle is repeatedly traveling on the same road as a vehicle outside information feature amount for estimation of the cognitive function of the driver. Note that, in this case, for example, the vehicle outside information is a vehicle outside captured image captured by the vehicle outside imaging device 5, and the vehicle outside information feature amount extracting unit 15 may determine that similar vehicle outside information is repeatedly output within the period on the basis of the vehicle outside captured images accumulated in the storage unit.

It is determined in advance what type of vehicle outside information feature amount the vehicle outside information feature amount extracting unit 15 extracts on the basis of the vehicle outside information. The vehicle outside information feature amount is determined in advance in such a way as to be information on a certain event that has occurred outside the vehicle and can cause a certain violation that is likely to be performed in a case where the driver is a driver with deteriorated cognitive function (see, for example, the homepage of the Tokyo police department, certain acts of violation (18 standard acts) that are likely to be performed when the cognitive function deteriorates, URL: "https://www.keishicho.metro.tokyo.jp/smph/menkyo/koshu/koureisha_anzen.html").

The vehicle outside information feature amount extracting unit 15 outputs the extracted vehicle outside information feature amount to the face information feature amount extracting unit 16, the biological information feature amount extracting unit 17, the vehicle information feature amount extracting unit 18, and the cognitive function estimation unit 19.

The face information feature amount extracting unit 16 extracts, in accordance with the vehicle outside information feature amount extracted by the vehicle outside information feature amount extracting unit 15, a face information feature amount for estimation of the cognitive function of the driver on the basis of the face information acquired by the face information acquiring unit 11. Details of the face information feature amount based on the vehicle outside information feature amount will be described later with a specific example. The face information feature amount extracting unit 16 outputs the extracted face information feature amount to the cognitive function estimation unit 19.

The biological information feature amount extracting unit 17 extracts, in accordance with the vehicle outside information feature amount extracted by the vehicle outside information feature amount extracting unit 15, a biological information feature amount for estimation of the cognitive function of the driver on the basis of the biological information acquired by the biological information acquiring unit 12. Details of the biological information feature amount based on the vehicle outside information feature amount will be described later with a specific example. The biological information feature amount extracting unit 17 outputs the extracted biological information feature amount to the cognitive function estimation unit 19.

The vehicle information feature amount extracting unit 18 extracts, in accordance with the vehicle outside information feature amount extracted by the vehicle outside information feature amount extracting unit 15, a vehicle information feature amount for estimation of the cognitive function of the driver on the basis of the vehicle information acquired by the vehicle information acquiring unit 13. Details of the vehicle information feature amount based on the vehicle outside information feature amount will be described later with a specific example. The vehicle information feature amount extracting unit 18 outputs the extracted vehicle information feature amount to the cognitive function estimation unit 19.

Here, the face information feature amount extracted by the face information feature amount extracting unit 16, the biological information feature amount extracted by the biological information feature amount extracting unit 17, or the vehicle information feature amount extracted by the vehicle information feature amount extracting unit 18, in accordance with the vehicle outside information feature amount extracted by the vehicle outside information feature amount extracting unit 15 will be described with specific examples.

FIG. 2 is a diagram for explaining a concept of an example of a relationship between the vehicle outside information feature amount extracted by the vehicle outside information feature amount extracting unit 15 and the face information feature amount extracted by the face information feature amount extracting unit 16, the biological information feature amount extracted by the biological information feature amount extracting unit 17, or the vehicle information feature amount extracted by the vehicle information feature amount extracting unit 18 in the first embodiment.

As illustrated in FIG. 2, what kind of face information feature amount the face information feature amount extracting unit 16 extracts, what kind of biological information feature amount the biological information feature amount extracting unit 17 extracts, or what kind of vehicle information feature amount the vehicle information feature amount extracting unit 18 extracts is determined in advance in accordance with the kind of the vehicle outside information feature amount extracted by the vehicle outside information feature amount extracting unit 15.

Note that, in FIG. 2, an example of the face information feature amount, an example of the biological information feature amount, or an example of the vehicle information feature amount that can be extracted in accordance with a certain vehicle outside information feature amount is listed and illustrated. For a certain vehicle outside information feature amount illustrated in FIG. 2, it is not essential that all of the face information feature amount, the biological information feature amount, and the vehicle information feature amount corresponding to the certain vehicle outside information feature amount illustrated in FIG. 2 are extracted. Specifically, FIG. 2 does not mean that, for example, in a case where information indicating that the traffic signal is red is extracted as the vehicle outside information feature amount, information indicating a line-of-sight direction of the driver and information indicating the face direction need to be necessarily extracted as the face information feature amount. In addition, FIG. 2 does not mean that, for example, in a case where information indicating that the traffic signal is red is extracted as the vehicle outside information feature amount, brake operation information indicating whether or not the brake is operated, the reaction time until the brake operation, and accelerator operation information indicating whether or not the accelerator is operated must be necessarily extracted.

For example, in a case where the vehicle outside information feature amount extracting unit 15 extracts information indicating that the traffic signal is red as the vehicle outside information feature amount, the face information feature amount extracting unit 16 extracts information indicating the line-of-sight direction of the driver as the face information feature amount on the basis of the face information acquired by the face information acquiring unit 11. In this case, for example, the vehicle information feature amount extracting unit 18 extracts brake operation information indicating whether or not the brake is operated as the vehicle information feature amount on the basis of the vehicle information acquired by the vehicle information acquiring unit 13. In this manner, the vehicle information feature amount extracting unit 18 can extract, as the vehicle information feature amount, information indicating an action pattern of the driver for the event indicated by the vehicle outside information feature amount. In the above-described example, the vehicle information feature amount extracting unit 18 sets, as the vehicle information feature amount, information indicating the action pattern of whether or not the driver has operated the brake for the event in which the traffic signal has turned to red, and which is indicated by the vehicle outside information feature amount.

On the basis of the vehicle information acquired by the vehicle information acquiring unit 13, the vehicle information feature amount extracting unit 18 may extract, as the vehicle information feature amount, a time required from when the vehicle outside information feature amount indicating that the traffic signal is red is extracted to when the brake is operated. For example, the vehicle information feature amount extracting unit 18 may calculate the time required from when the vehicle outside information feature amount indicating that the traffic signal is red is extracted to when the brake is operated on the basis of the vehicle information accumulated in the storage unit. As described above, the vehicle information feature amount extracting unit 18 can set, as the vehicle information feature amount, the reaction time of the driver for the event indicated by the vehicle outside information feature amount. In the above-described example, the vehicle information feature amount extracting unit 18 sets, as the vehicle information feature amount, the reaction time until the driver operates the brake for the event in which the traffic signal has turned to red, and which is indicated by the vehicle outside information feature amount.

In addition, for example, in a case where the vehicle outside information feature amount extracting unit 15 extracts information indicating that the traffic signal is green as the vehicle outside information feature amount, the face information feature amount extracting unit 16 extracts information indicating a line-of-sight direction of the driver as the face information feature amount on the basis of the face information acquired by the face information acquiring unit 11. In this case, for example, the vehicle information feature amount extracting unit 18 extracts accelerator operation information indicating whether or not the accelerator is operated as the vehicle information feature amount on the basis of the vehicle information acquired by the vehicle information acquiring unit 13. For example, the vehicle information feature amount extracting unit 18 may extract, as the vehicle information feature amount, a reaction time from when the vehicle outside information feature amount indicating that the traffic signal is green is extracted to when the accelerator is operated.

Furthermore, for example, in a case where the vehicle outside information feature amount extracting unit 15 extracts information indicating that there is running out as the vehicle outside information feature amount, the face information feature amount extracting unit 16 extracts information indicating the eye-opening degree of the driver as the face information feature amount on the basis of the face information acquired by the face information acquiring unit 11. In this case, for example, the vehicle information feature amount extracting unit 18 extracts, as the vehicle information feature amount, a time required from when the vehicle outside information feature amount indicating that there is running out is extracted to when the brake is operated, on the basis of the vehicle information acquired by the vehicle information acquiring unit 13.

Furthermore, for example, in a case where the vehicle outside information feature amount extracting unit 15 extracts information indicating that there is a traffic sign for a temporary stop as the vehicle outside information feature amount, the vehicle information feature amount extracting unit 18 extracts brake operation information indicating whether or not the brake has been operated as the vehicle information feature amount on the basis of the vehicle information acquired by the vehicle information acquiring unit 13.

Furthermore, for example, in a case where the vehicle outside information feature amount extracting unit 15 extracts information indicating that the vehicle is repeatedly traveling on the same road as the vehicle outside information feature amount, the face information feature amount extracting unit 16 extracts emotion information of the driver as the face information feature amount on the basis of the face information acquired by the face information acquiring unit 11. In this case, for example, the biological information feature amount extracting unit 17 extracts information on the pulse and the heart rate of the driver as the biological information feature amount on the basis of the biological information acquired by the biological information acquiring unit 12. In addition, in this case, for example, the vehicle information feature amount extracting unit 18 extracts information indicating whether or not the navigation device has been operated as the vehicle information feature amount on the basis of the vehicle information acquired by the vehicle information acquiring unit 13.

Although not illustrated in FIG. 2, for example, when the vehicle outside information feature amount extracting unit 15 extracts information indicating that the vehicle is traveling at an intersection or a curve as the vehicle outside information feature amount, the vehicle information feature amount extracting unit 18 may extract the steering wheel steering angle of the vehicle as the vehicle information feature amount on the basis of the vehicle information acquired by the vehicle information acquiring unit 13.

In the above example, in the cognitive function estimation device 1, the example in which the vehicle information feature amount extracting unit 18 extracts the information indicating the action pattern of the driver for the event indicated by the vehicle outside information feature amount as the vehicle information feature amount has been described. In addition to this, in the cognitive function estimation device 1, the face information feature amount extracting unit 16 can also extract information indicating an action pattern of the driver as the face information feature amount. For example, in a case where the vehicle outside information feature amount extracting unit 15 extracts information indicating that there is running out as the vehicle outside information feature amount, the face information feature amount extracting unit 16 can also set, as the face information feature amount, information indicating an action pattern indicating whether or not the emotion information of the driver has changed for the event in which there is the running out, on the basis of the face information accumulated in the storage unit. For example, in a case where there is no change in the emotion information of the driver, it can be said that the driver has taken an action of continuing being expressionless for the event in which there is the running out, without noticing the running out.

Furthermore, for example, in a case where the vehicle outside information feature amount extracting unit 15 extracts information indicating that there is a traffic sign for a temporary stop as the vehicle outside information feature amount, the face information feature amount extracting unit 16 can also set, as the face information feature amount, information indicating an action pattern in which the driver has changed the line-of-sight direction for an event in which there is the traffic sign for a temporary stop, on the basis of the face information accumulated in the storage unit. For example, when the driver does not direct his/her line of sight at the direction of the traffic sign for a temporary stop, it can be said that the driver has taken an action of overlooking the traffic sign.

In addition, in the cognitive function estimation device 1, the biological information feature amount extracting unit 17 can also extract information indicating the action pattern of the driver as the biological information feature amount. For example, in a case where the vehicle outside information feature amount extracting unit 15 extracts information indicating that there is running out as the vehicle outside information feature amount, the biological information feature amount extracting unit 17 can also set, as the biological information feature amount, information indicating an action pattern indicating whether or not the respiratory rate of the driver has changed for the event in which there is the running out, on the basis of the biological information accumulated in the storage unit. For example, in a case where the respiratory rate of the driver has changed to increase, it can be said that the driver intentionally has taken an action of taking a large amount of breathing for the event in which there is the running out, in order to calm down.

In the above example, in the cognitive function estimation device 1, the example has been described in which the vehicle information feature amount extracting unit 18 extracts the reaction time from the occurrence of the event indicated by the vehicle outside information feature amount to the vehicle operation performed by the driver as the vehicle information feature amount. In addition to this, in the cognitive function estimation device 1, the face information feature amount extracting unit 16 can also extract, as the face information feature amount, a reaction time from occurrence of the event indicated by the vehicle outside information feature amount to occurrence of a change in the face information of the driver. For example, in a case where the vehicle outside information feature amount extracting unit 15 extracts information indicating that the traffic signal is red as the vehicle outside information feature amount, the face information feature amount extracting unit 16 can also set, as the face information feature amount, a reaction time until the driver directs his/her line of sight to the red traffic signal on the basis of the face information accumulated in the storage unit.

Furthermore, in the cognitive function estimation device 1, the biological information feature amount extracting unit 17 can also extract, as the biological information feature amount, a reaction time from occurrence of the event indicated by the vehicle outside information feature amount to occurrence of a change in the biological information of the driver. For example, in a case where the vehicle outside information feature amount extracting unit 15 extracts information indicating that running out has occurred as the vehicle outside information feature amount, the biological information feature amount extracting unit 17 can also set, as the biological information feature amount, a reaction time until occurrence of a change in the respiratory rate of the driver for the event in which the running out has occurred, on the basis of the biological information accumulated in the storage unit.

In this manner, the face information feature amount extracting unit 16, the biological information feature amount extracting unit 17, or the vehicle information feature amount extracting unit 18 extracts the face information feature amount, the biological information feature amount, or the vehicle information feature amount respectively in accordance with the vehicle outside information feature amount extracted by the vehicle outside information feature amount extracting unit 15.

As the face information feature amount, the biological information feature amount, or the vehicle information feature amount, information for discriminating a certain violation that is likely to be performed in a case where the driver is a driver with a deteriorated cognitive function is set in accordance with the vehicle outside information feature amount.

Note that, as described above, it is not essential for the cognitive function estimation device 1 to extract all of the face information feature amount, the biological information feature amount, and the vehicle information feature amount with respect to the vehicle outside information feature amount extracted by the vehicle outside information feature amount extracting unit 15. The cognitive function estimation device 1 only needs to extract at least one of the face information feature amount, the biological information feature amount, or the vehicle information feature amount with respect to the vehicle outside information feature amount extracted by the vehicle outside information feature amount extracting unit 15.

Returning to the description of the cognitive function estimation device 1 using FIG. 1.

The cognitive function estimation unit 19 estimates whether or not the cognitive function of the driver is low on the basis of the machine learning model 203, the vehicle outside information feature amount extracted by the vehicle outside information feature amount extracting unit 15, and at least one of the vehicle information feature amount extracted by the vehicle information feature amount extracting unit 18, the face information feature amount extracted by the face information feature amount extracting unit 16, or the biological information feature amount extracted by the biological information feature amount extracting unit 17. Specifically, the cognitive function estimation unit 19 inputs the vehicle outside information feature amount, and at least one of the vehicle information feature amount, the face information feature amount, or the biological information feature amount to the machine learning model 203, and thereby obtains cognitive function information indicating whether or not the cognitive function of the driver is low.

In the first embodiment, it is assumed that the cognitive function estimation unit 19 includes the determination unit 191.

The determination unit 191 of the cognitive function estimation unit 19 determines whether or not the cognitive function of the driver is estimated to be low continually in a preset period (hereinafter, referred to as a "determination period") on the basis of the machine learning model 203, the vehicle outside information feature amount extracted by the vehicle outside information feature amount extracting unit 15, and at least one of the vehicle information feature amount extracted by the vehicle information feature amount extracting unit 18, the face information feature amount extracted by the face information feature amount extracting unit 16, or the biological information feature amount extracted by the biological information feature amount extracting unit 17.

When the determination unit 191 determines that the cognitive function of the driver is estimated to be low continually in the determination period, the cognitive function estimation unit 19 estimates that the cognitive function of the driver is low. As a result, it is possible to prevent the cognitive function of the driver from being instantaneously estimated to be low, and thus it is possible to improve the estimation accuracy of the cognitive function of the driver.

Note that, here, it is assumed that the cognitive function estimation unit 19 includes the determination unit 191, but this is merely an example. The cognitive function estimation unit 19 may be configured not to include the determination unit 191.

The learning device 20 generates the machine learning model 203 that receives, as input, the vehicle outside information feature amount for estimation of the cognitive function of the driver of the vehicle, and at least one of the vehicle information feature amount which is for estimation of the cognitive function of the driver of the vehicle and which is corresponding to the vehicle outside information feature amount, the face information feature amount which is for estimation of the cognitive function of the driver of the vehicle and which is corresponding to the vehicle outside information feature amount, or the biological information feature amount which is for estimation of the cognitive function of the driver of the vehicle and which is corresponding to the vehicle outside information feature amount, and outputs the cognitive function information indicating whether or not the cognitive function of the driver is low. Note that the machine learning model 203 is generated by the learning device 20 before the cognitive function estimation unit 19 estimates the cognitive function of the driver.

The learning device 20 includes the acquisition unit 201, the learning unit 202, and the machine learning model 203.

The acquisition unit 201 acquires a vehicle outside information feature amount, and a vehicle information feature amount, a face information feature amount, or a biological information feature amount, which are input to the machine learning model 203. Correct answer information indicating whether or not the cognitive function is low is attached to the vehicle outside information feature amount, and the vehicle information feature amount, the face information feature amount, or the biological information feature amount acquired by the acquisition unit 201.

The vehicle outside information feature amount, and the vehicle information feature amount, the face information feature amount, or the biological information feature amount to which the correct answer information is attached, and which are input to the machine learning model 203, are generated in advance. The acquisition unit 201 acquires the vehicle outside information feature amount, and the vehicle information feature amount, the face information feature amount, or the biological information feature amount generated in advance.

Note that the specific content of the vehicle outside information feature amount, the vehicle information feature amount, the face information feature amount, or the biological information feature amount acquired by the acquisition unit 201 is similar to the specific content of the vehicle outside information feature amount extracted by the vehicle outside information feature amount extracting unit 15, the face information feature amount extracted by the face information feature amount extracting unit 16, the biological information feature amount extracted by the biological information feature amount extracting unit 17, or the vehicle information feature amount extracted by the vehicle information feature amount extracting unit 18.

For example, an administrator or the like conducts a paper test on a subject and measures the cognitive function of the subject, thereby collecting test travel data of the subject. For example, the administrator or the like may collect test travel data of the subject by causing the subject to perform test travel and measuring the cognitive function of the subject. The administrator or the like generates, from the collected test travel data, a vehicle outside information feature amount, and a vehicle information feature amount, a face information feature amount, or a biological information feature amount to which correct answer information is attached, and which are input to the machine learning model 203. Note that the administrator or the like desirably sets a certain number of drivers of vehicles having various levels of cognitive functions as subjects.

For example, as the vehicle outside information feature amount, the vehicle information feature amount, the face information feature amount, or the biological information feature amount acquired by the acquisition unit 201, the vehicle outside information feature amount, the vehicle information feature amount, the face information feature amount, or the biological information feature amount when a normal person drives the vehicle, and the vehicle outside information feature amount, the vehicle information feature amount, the face information feature amount, or the biological information feature amount when a person with a low cognitive function drives the vehicle are generated in advance. Correct answer information indicating that the cognitive function is not low is attached to the vehicle outside information feature amount, the vehicle information feature amount, the face information feature amount, or the biological information feature amount when a normal person drives the vehicle. On the other hand, correct answer information indicating that the cognitive function is low is attached to the vehicle outside information feature amount, the vehicle information feature amount, the face information feature amount, or the biological information feature amount when a person with a low cognitive function drives the vehicle.

Specifically, for example, a vehicle outside information feature amount, a vehicle information feature amount, a face information feature amount, or a biological information feature amount acquired when each of a normal person and an elderly person with a low cognitive function who perform test travel of the vehicle performs the test travel is generated in advance. Note that, in the first embodiment, a normal person refers to a person having a cognitive function necessary for appropriately driving a vehicle. On the other hand, a person with a low cognitive function refers to a person who does not have a cognitive function sufficient for appropriately driving a vehicle.

A vehicle outside information feature amount, a vehicle information feature amount, a face information feature amount, or a biological information feature amount acquired when each of a normal person and a driver with a low cognitive function, such as an elderly person, performs the test travel will be described with specific examples.

For example, it is assumed that a traffic signal has changed to red when a normal person performs the test travel. Then, the normal person visually recognizes the red traffic signal and instantaneously operates the brake to stop the vehicle. In this case, information indicating that the traffic signal is red is generated as the vehicle outside information feature amount. In addition, a line-of-sight direction of the normal person when the traffic signal turns to red is generated as the face information feature amount. Further, whether or not the normal person has performed the brake operation after the traffic signal turns to red and the reaction time from when the traffic signal turns to red to the brake operation are generated as the vehicle information feature amount. Then, correct answer information indicating that the cognitive function is not low is attached to the vehicle outside information feature amount, the face information feature amount, and the vehicle information feature amount.

On the other hand, for example, it is assumed that the traffic signal has changed to red when an elderly person with a low cognitive function performs the test travel. Then, for example, the elderly person visually recognizes the red traffic signal and operates the brake to stop the vehicle, but it takes a longer time for the elderly person to operate the brake than the time until the normal person operates the brake. In this case, information indicating that the traffic signal is red is generated as the vehicle outside information feature amount. In addition, a line-of-sight direction of the elderly person when the traffic signal has changed to red is generated as the face information feature amount. In addition, whether or not the elderly person has performed the brake operation after the traffic signal changed to red and the reaction time from when the traffic signal has changed to red to the brake operation are generated as the vehicle information feature amount. Then, correct answer information indicating that the cognitive function is low is attached to the vehicle outside information feature amount, the face information feature amount, and the vehicle information feature amount.

The acquisition unit 201 outputs the acquired vehicle outside information feature amount, and the acquired vehicle information feature amount, the acquired face information feature amount, or the acquired biological information feature amount to the learning unit 202.

The learning unit 202 generates the machine learning model 203 by learning using the vehicle outside information feature amount acquired by the acquisition unit 201, and the vehicle information feature amount acquired by the acquisition unit 201, the face information feature amount acquired by the acquisition unit 201, or the biological information feature amount acquired by the acquisition unit 201.

Note that, in the first embodiment, as illustrated in FIG. 1, it is assumed that the learning device 20 is included in the cognitive function estimation device 1, but this is merely an example. The learning device 20 may be provided outside the cognitive function estimation device 1 in a place that can be referred to by the cognitive function estimation device 1, or the learning device 20 may be used alone.

An operation of the cognitive function estimation device 1 according to the first embodiment will be described.

FIG. 3 is a flowchart for explaining the operation of the cognitive function estimation device 1 according to the first embodiment.

The cognitive function estimation device 1 performs information acquisition processing and thereby acquires various types of information (step ST301). Specifically, the face information acquiring unit 11 acquires a vehicle inside captured image from the vehicle inside imaging device 2, and acquires face information on the face of the driver of the vehicle on the basis of the vehicle inside captured image. Further, the biological information acquiring unit 12 acquires biological information of the driver of the vehicle from the biological sensor 3. In addition, the vehicle information acquiring unit 13 acquires vehicle information on the vehicle from the vehicle information detection device 4. Furthermore, the vehicle outside information acquiring unit 14 acquires a vehicle outside captured image from the vehicle outside imaging device 5, and acquires vehicle outside information on the situation around the vehicle on the basis of the vehicle outside captured image.

The face information acquiring unit 11 outputs the acquired face information to the face information feature amount extracting unit 16. In addition, the biological information acquiring unit 12 outputs the acquired biological information to the biological information feature amount extracting unit 17. In addition, the vehicle information acquiring unit 13 outputs the acquired vehicle information to the vehicle information feature amount extracting unit 18. Furthermore, the vehicle outside information acquiring unit 14 outputs the acquired vehicle outside information to the vehicle outside information feature amount extracting unit 15.

The vehicle outside information feature amount extracting unit 15 extracts a vehicle outside information feature amount for estimation of the cognitive function of the driver on the basis of the vehicle outside information acquired by the vehicle outside information acquiring unit 14 in step ST301 (step ST302).

The vehicle outside information feature amount extracting unit 15 outputs the extracted vehicle outside information feature amount to the face information feature amount extracting unit 16, the biological information feature amount extracting unit 17, the vehicle information feature amount extracting unit 18, and the cognitive function estimation unit 19.

The cognitive function estimation device 1 performs various feature amount extraction processing in accordance with the vehicle outside information feature amount extracted by the vehicle outside information feature amount extracting unit 15 in step ST302 (step ST303).

Specifically, the face information feature amount extracting unit 16 extracts, in accordance with the vehicle outside information feature amount extracted by the vehicle outside information feature amount extracting unit 15, a face information feature amount for estimation of the cognitive function of the driver on the basis of the face information acquired by the face information acquiring unit 11. In addition, the biological information feature amount extracting unit 17 extracts, in accordance with the vehicle outside information feature amount extracted by the vehicle outside information feature amount extracting unit 15, a biological information feature amount for estimation of the cognitive function of the driver on the basis of the biological information acquired by the biological information acquiring unit 12. In addition, the vehicle information feature amount extracting unit 18 extracts, in accordance with the vehicle outside information feature amount extracted by the vehicle outside information feature amount extracting unit 15, a vehicle information feature amount for estimation of the cognitive function of the driver on the basis of the vehicle information acquired by the vehicle information acquiring unit 13.

The face information feature amount extracting unit 16 outputs the extracted face information feature amount to the cognitive function estimation unit 19. In addition, the biological information feature amount extracting unit 17 outputs the extracted biological information feature amount to the cognitive function estimation unit 19. In addition, the vehicle information feature amount extracting unit 18 outputs the extracted vehicle information feature amount to the cognitive function estimation unit 19.

The cognitive function estimation device 1 performs cognitive function estimation processing (step ST304). Specifically, the cognitive function estimation unit 19 estimates whether or not the cognitive function of the driver is low on the basis of the machine learning model 203, the vehicle outside information feature amount extracted by the vehicle outside information feature amount extracting unit 15 in step ST302, and at least one of the vehicle information feature amount extracted by the vehicle information feature amount extracting unit 18 in step ST303, the face information feature amount extracted by the face information feature amount extracting unit 16 in step ST303, or the biological information feature amount extracted by the biological information feature amount extracting unit 17 in step ST303.

FIG. 4 is a flowchart for explaining the operation of the learning device 20 according to the first embodiment.

The acquisition unit 201 performs feature amount acquisition processing (step ST401). Specifically, the acquisition unit 201 acquires a vehicle outside information feature amount and a vehicle information feature amount, a face information feature amount, or a biological information feature amount, to which correct answer information is attached, and which are input to the machine learning model 203.

The acquisition unit 201 outputs the acquired vehicle outside information feature amount and the vehicle information feature amount, the face information feature amount, or the biological information feature amount to the learning unit 202.

The learning unit 202 generates the machine learning model 203 by learning using the vehicle outside information feature amount and the vehicle information feature amount, the face information feature amount, or the biological information feature amount acquired by the acquisition unit 201 in step ST401 (step ST402).

As described above, the cognitive function estimation device 1 according to the first embodiment extracts the vehicle outside information feature amount for estimating that the cognitive function of the driver is deteriorated, and extracts, in accordance with the extracted vehicle outside information feature amount, the face information feature amount, the biological information feature amount, or the vehicle information feature amount for estimating that the cognitive function of the driver is deteriorated. Then, the cognitive function estimation device 1 inputs the extracted vehicle outside information feature amount and the extracted face information feature amount, the extracted biological information feature amount, or the extracted vehicle information feature amount to the machine learning model 203, and thereby obtains cognitive function information indicating whether or not the cognitive function of the driver is low.

As described above, the cognitive function estimation device 1 can estimate the cognitive function as to whether or not the driver can constantly appropriately drive the vehicle.

The cognitive function information obtained in the cognitive function estimation device 1 according to the first embodiment can be used in various scenes.

For example, it is assumed that the vehicle is an autonomous driving vehicle that can automatically travel without a person performing a driving operation, and the cognitive function estimation device 1 is mounted on the autonomous driving vehicle. In this case, when the cognitive function estimation device 1 obtains the cognitive function information indicating that the cognitive function of a driver is low, driving assistance such as enhancing the effect of the brake of the vehicle driven by the driver or enhancing the effect of the operation of the steering wheel can be performed on the basis of the cognitive function information.

Furthermore, for example, a medical institution can use the cognitive function information as a basis for making decisions about whether or not to permit driving by a driver.

In addition, for example, a person with a deteriorated cognitive function may undergo rehabilitation to recover the cognitive function by driving. If the cognitive function estimation device 1 is mounted on a vehicle used in such rehabilitation, the cognitive function information obtained by the cognitive function estimation device 1 can help confirm the result of the rehabilitation.

In addition, for example, in a case where the cognitive function estimation device 1 obtains the cognitive function information indicating that the cognitive function of a driver is low, it is also possible to provide notification that the cognitive function of the driver of a vehicle is low from the vehicle to the surroundings on the basis of the cognitive function information. Specifically, for example, a control unit (not illustrated) provided in the cognitive function estimation device 1 transmits an email providing notification that the driver is driving to a family member of the driver. Furthermore, for example, the control unit performs control to turn on the hazard lights or sound the horn.

Figure 5A:
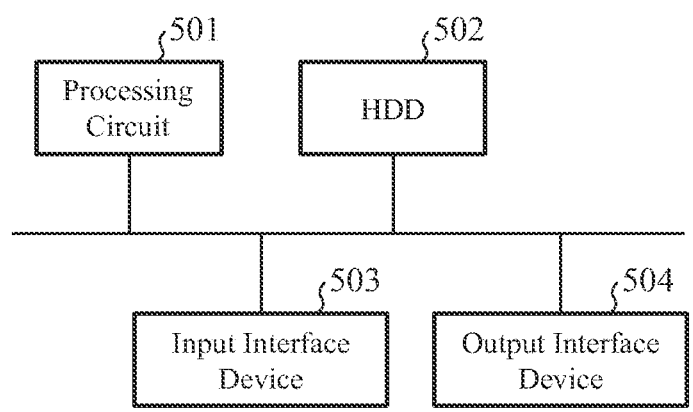
FIGS. 5A and 5B are diagrams each showing an example of a hardware configuration of the cognitive function estimation device according to the first embodiment.
Figure 5B:
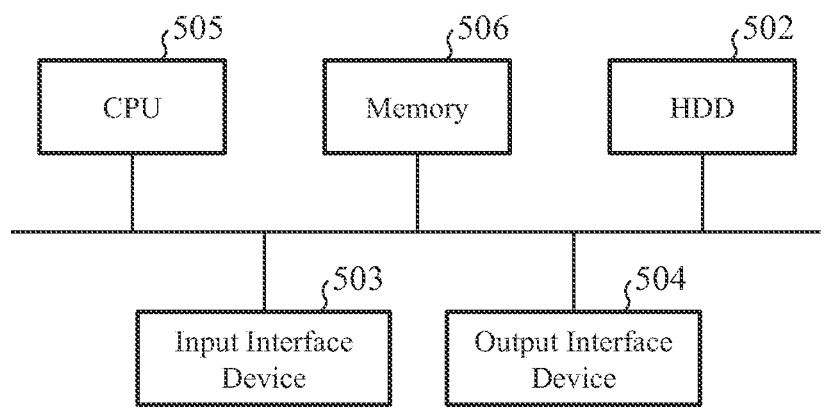

FIGS. 5A and 5B are diagrams each showing an example of the hardware configuration of the cognitive function estimation device 1 according to the first embodiment.

In the first embodiment, the functions of the face information acquiring unit 11, the biological information acquiring unit 12, the vehicle information acquiring unit 13, the vehicle outside information acquiring unit 14, the vehicle outside information feature amount extracting unit 15, the face information feature amount extracting unit 16, the biological information feature amount extracting unit 17, the vehicle information feature amount extracting unit 18, the cognitive function estimation unit 19, the acquisition unit 201, and the learning unit 202 are implemented by a processing circuit 501. That is, the cognitive function estimation device 1 includes the processing circuit 501 for inferring the cognitive function of a driver.

The processing circuit 501 may be dedicated hardware as shown in FIG. 5A, or may be a central processing unit (CPU) 505 which executes a program stored in a memory 506 as shown in FIG. 5B.

In a case where the processing circuit 501 is dedicated hardware, the processing circuit 501 may be, for example, a single circuit, a composite circuit, a programmed processor, a parallel-programmed processor, an application specific integrated circuit (ASIC), a field-programmable gate array (FPGA), or a combination thereof.

When the processing circuit 501 is the CPU 505, the functions of the face information acquiring unit 11, the biological information acquiring unit 12, the vehicle information acquiring unit 13, the vehicle outside information acquiring unit 14, the vehicle outside information feature amount extracting unit 15, the face information feature amount extracting unit 16, the biological information feature amount extracting unit 17, the vehicle information feature amount extracting unit 18, the cognitive function estimation unit 19, the acquisition unit 201, and the learning unit 202 are implemented by software, firmware, or a combination of software and firmware. That is, the face information acquiring unit 11, the biological information acquiring unit 12, the vehicle information acquiring unit 13, the vehicle outside information acquiring unit 14, the vehicle outside information feature amount extracting unit 15, the face information feature amount extracting unit 16, the biological information feature amount extracting unit 17, the vehicle information feature amount extracting unit 18, the cognitive function estimation unit 19, the acquisition unit 201, and the learning unit 202 are implemented by the processing circuit 501 such as the CPU 505 or a system large-scale integration (LSI) that executes a program stored in a hard disk drive (HDD) 502, the memory 506, or the like. Further, it can also be said that the program stored in the HDD 502, the memory 506, or the like causes a computer to execute procedures or methods performed by the face information acquiring unit 11, the biological information acquiring unit 12, the vehicle information acquiring unit 13, the vehicle outside information acquiring unit 14, the vehicle outside information feature amount extracting unit 15, the face information feature amount extracting unit 16, the biological information feature amount extracting unit 17, the vehicle information feature amount extracting unit 18, the cognitive function estimation unit 19, the acquisition unit 201, and the learning unit 202. Here, the memory 506 is, for example, a nonvolatile or volatile semiconductor memory, such as a random access memory (RAM), a read only memory (ROM), a flash memory, an erasable programmable read only memory (EPROM), and an electrically erasable programmable read only memory (EEPROM), a magnetic disk, a flexible disk, an optical disk, a compact disk, a mini disk, a digital versatile disc (DVD), or the like.

Note that a part of the functions of the face information acquiring unit 11, the biological information acquiring unit 12, the vehicle information acquiring unit 13, the vehicle outside information acquiring unit 14, the vehicle outside information feature amount extracting unit 15, the face information feature amount extracting unit 16, the biological information feature amount extracting unit 17, the vehicle information feature amount extracting unit 18, the cognitive function estimation unit 19, the acquisition unit 201, and the learning unit 202 may be implemented by dedicated hardware, and another part thereof may be implemented by software or firmware. For example, the functions of the biological information acquiring unit 12, the vehicle information acquiring unit 13, and the vehicle outside information acquiring unit 14 can be implemented by the processing circuit 501 as dedicated hardware, and the functions of the vehicle outside information feature amount extracting unit 15, the face information feature amount extracting unit 16, the biological information feature amount extracting unit 17, the vehicle information feature amount extracting unit 18, the cognitive function estimation unit 19, the acquisition unit 201, and the learning unit 202 can be implemented by the processing circuit 501 reading and executing the program stored in the memory 506.

In addition, the machine learning model 203 uses the memory 506. Note that this is an example, and the machine learning model 203 may be configured by the HDD 502, a solid state drive (SSD), a DVD, or the like.

In addition, the cognitive function estimation device 1 includes an input interface device 503 and an output interface device 504 that perform wired communication or wireless communication with a device such as the vehicle inside imaging device 2, the biological sensor 3, the vehicle information detection device 4, or the vehicle outside imaging device 5.

As described above, according to the first embodiment, the cognitive function estimation device 1 includes: the vehicle outside information acquiring unit 14 to acquire vehicle outside information on a situation around the vehicle; the face information acquiring unit 11 to acquire face information on the face of a driver of the vehicle; the biological information acquiring unit 12 to acquire biological information of the driver; the vehicle information acquiring unit 13 to acquire vehicle information on the vehicle; the vehicle outside information feature amount extracting unit 15 to extract a vehicle outside information feature amount for estimation of a cognitive function of the driver on the basis of the vehicle outside information acquired by the vehicle outside information acquiring unit 14; the face information feature amount extracting unit 16 to extract, in accordance with the vehicle outside information feature amount extracted by the vehicle outside information feature amount extracting unit 15, a face information feature amount for estimation of the cognitive function of the driver on the basis of the face information acquired by the face information acquiring unit 11; the biological information feature amount extracting unit 17 to extract, in accordance with the vehicle outside information feature amount extracted by the vehicle outside information feature amount extracting unit 15, a biological information feature amount for estimation of the cognitive function of the driver on the basis of the biological information acquired by the biological information acquiring unit 12; the vehicle information feature amount extracting unit 18 to extract, in accordance with the vehicle outside information feature amount extracted by the vehicle outside information feature amount extracting unit 15, a vehicle information feature amount for estimation of the cognitive function of the driver on the basis of the vehicle information acquired by the vehicle information acquiring unit 13; and the cognitive function estimation unit 19 to estimate whether or not the cognitive function of the driver is low on the basis of the machine learning model 203, the vehicle outside information feature amount extracted by the vehicle outside information feature amount extracting unit 15, and at least one of the face information feature amount extracted by the face information feature amount extracting unit 16, the biological information feature amount extracted by the biological information feature amount extracting unit 17, or the vehicle information feature amount extracted by the vehicle information feature amount extracting unit 18. Therefore, it is possible to estimate whether or not the driver has a certain level of cognitive function.

Further, in addition to the above configuration, the cognitive function estimation device 1 according to the first embodiment includes the determination unit 191 to determine whether or not the cognitive function of the driver is estimated to be low continually in the determination period on the basis of the machine learning model 203, the vehicle outside information feature amount, and at least one of the face information feature amount, the biological information feature amount, or the vehicle information feature amount. Then, when the determination unit 191 determines that the cognitive function of the driver is estimated to be low continually in the determination period, the cognitive function estimation unit 19 estimates that the cognitive function of the driver is low. As a result, the cognitive function estimation device 1 can prevent the cognitive function of the driver from being instantaneously estimated to be low, and thus can improve the estimation accuracy of the cognitive function of the driver.

In the first embodiment described above, it is assumed that the cognitive function estimation device 1 is an in-vehicle device mounted on a vehicle, and the face information acquiring unit 11, the biological information acquiring unit 12, the vehicle information acquiring unit 13, the vehicle outside information acquiring unit 14, the vehicle outside information feature amount extracting unit 15, the face information feature amount extracting unit 16, the biological information feature amount extracting unit 17, the vehicle information feature amount extracting unit 18, the cognitive function estimation unit 19, and the learning device 20 are included in the cognitive function estimation device 1.

Not limited to this, an in-vehicle device and a server may constitute a cognitive function estimation system in such a manner that a part of the face information acquiring unit 11, the biological information acquiring unit 12, the vehicle information acquiring unit 13, the vehicle outside information acquiring unit 14, the vehicle outside information feature amount extracting unit 15, the face information feature amount extracting unit 16, the biological information feature amount extracting unit 17, the vehicle information feature amount extracting unit 18, the cognitive function estimation unit 19, and the learning device 20 is included in the in-vehicle device mounted on a vehicle, and the others are included in the server connected to the in-vehicle device via a network.

It should be noted that the invention of the present application is capable of modifying any of the components of the embodiment or omitting any of the components of the embodiment within the scope of the invention.

INDUSTRIAL APPLICABILITY

Since the cognitive function estimation device according to the present invention is configured to be able to estimate whether or not a driver has a certain level of cognitive function, the cognitive function estimation device can be applied to a cognitive function estimation device that estimates the cognitive function of a driver of a vehicle.

REFERENCE SIGNS LIST

1: cognitive function estimation device, 2: vehicle inside imaging device, 3: biological sensor, 4: vehicle information detection device, 5: vehicle outside imaging device, 11: face information acquiring unit, 12: biological information acquiring unit, 13: vehicle information acquiring unit, 14: vehicle outside information acquiring unit, 15: vehicle outside information feature amount extracting unit, 16: face information feature amount extracting unit, 17: biological information feature amount extracting unit, 18: vehicle information feature amount extracting unit, 19: cognitive function estimation unit, 191: determination unit, 20: learning device, 201: acquisition unit, 202: learning unit, 203: machine learning model, 501: processing circuit, 502: HDD, 503: input interface device, 504: output interface device, 505: CPU, 506: memory

The invention claimed is:

1. A cognitive function estimation device, comprising: processing circuitry
to acquire vehicle outside information on a situation around a vehicle;
to acquire face information on a face of a driver of the vehicle;
to acquire biological information of the driver;
to acquire vehicle information on the vehicle;
to extract a vehicle outside information feature amount for estimation of a cognitive function of the driver on a basis of the vehicle outside information acquired;
to extract, in accordance with the vehicle outside information feature amount extracted, a face information feature amount for the estimation of the cognitive function of the driver on a basis of the face information acquired;
to extract, in accordance with the vehicle outside information feature amount extracted, a to extract, in accordance with the vehicle outside information feature amount extracted, a biological information feature amount for the estimation of the cognitive function of the driver on a basis of the biological information acquired;
to extract, in accordance with the vehicle outside information feature amount extracted, a to extract, in accordance with the vehicle outside information feature amount extracted, a vehicle information feature amount for the estimation of the cognitive function of the driver on a basis of the vehicle information acquired; and
to estimate whether or not the cognitive function of the driver is low on a basis of a machine learning model, the vehicle outside information feature amount extracted, and at least one of the face information feature amount extracted, the biological information feature amount extracted, or the vehicle information feature amount extracted,
wherein, in response to extracting a first vehicle outside information feature amount, the processing circuitry extracts the face information feature amount without extracting the biological information feature amount, and
wherein, in response to extracting a second vehicle outside information feature amount, the processing circuitry extracts both of the face information feature amount and the biological information feature amount.

2. The cognitive function estimation device according to claim 1, wherein
the processing circuitry determines whether or not the cognitive function of the driver is estimated to be low continually in a determination period on a basis of the machine learning model, the vehicle outside information feature amount, and at least one of the face information feature amount, the biological information feature amount, or the vehicle information feature amount, and
when it is determined that the cognitive function of the driver is estimated to be low continually in the determination period, the processing circuitry estimates that the cognitive function of the driver is low.

3. The cognitive function estimation device according to claim 1, wherein the face information feature amount includes information on a line of sight of the driver, information on an eye-opening degree of the driver, or information on an emotion of the driver.

4. The cognitive function estimation device according to claim 1, wherein the vehicle information feature amount includes information on an accelerator operation amount of the driver, information on a brake operation amount of the driver, or information on a steering wheel operation amount of the driver.

5. The cognitive function estimation device according to claim 1, wherein the vehicle information feature amount, the face information feature amount, or the biological information feature amount is a reaction time of the driver for an event represented by the vehicle outside information feature amount.

6. The cognitive function estimation device according to claim 1, wherein the vehicle information feature amount, the face information feature amount, or the biological information feature amount is information indicating an action pattern of the driver for an event represented by the vehicle outside information feature amount.

7. The cognitive function estimation device according to claim 1, wherein the machine learning model is generated by learning a vehicle outside information feature amount for the estimation of the cognitive function of the driver, and at least one of a face information feature amount which is for the estimation of the cognitive function of the driver and which is corresponding to the vehicle outside information feature amount, a biological information feature amount which is for the estimation of the cognitive function of the driver and which is corresponding to the vehicle outside information feature amount, or a vehicle information feature amount which is for the estimation of the cognitive function of the driver and which is corresponding to the vehicle outside information feature amount.

8. A learning device comprising:
processing circuitry
to acquire a vehicle outside information feature amount for estimation of a cognitive function of a driver of a vehicle, and at least one of a face information feature amount which is for the estimation of the cognitive function of the driver of the vehicle and which is corresponding to the vehicle outside information feature amount, a biological information feature amount which is for the estimation of the cognitive function of the driver of the vehicle and which is corresponding to the vehicle outside information feature amount, or a vehicle information feature amount which is for the estimation of the cognitive function of the driver of the vehicle and which is corresponding to the vehicle outside information feature amount; and to receive, as inputs, the vehicle outside information feature amount, and at least one of the face information feature amount, the biological information feature amount, or the vehicle information feature amount acquired, and thereby generate a machine learning model that outputs cognitive function information indicating whether or not the cognitive function of the driver of the vehicle is low, wherein, in response to acquiring a first vehicle outside information feature amount, the processing circuitry acquires the face information feature amount without acquiring the biological information feature amount, and wherein, in response to acquiring a second vehicle outside information feature amount, the processing circuitry acquires both of the face information feature amount and the biological information feature amount.

9. The learning device according to claim 8, wherein the vehicle outside information feature amount, the vehicle information feature amount, the face information feature amount, or the biological information feature amount acquired includes: a vehicle outside information feature amount, a vehicle information feature amount, a face information feature amount, or a biological information feature amount when a normal person drives the vehicle; and a vehicle outside information feature amount, a vehicle information feature amount, a face information feature amount, or a biological information feature amount when a person with a low cognitive function drives the vehicle.

10. A cognitive function estimation method, comprising:
acquiring vehicle outside information on a situation around a vehicle;
acquiring face information on a face of a driver of the vehicle;
acquiring biological information of the driver;
acquiring vehicle information on the vehicle;
extracting a vehicle outside information feature amount for estimation of a cognitive function of the driver on a basis of the vehicle outside information acquired;
extracting, in accordance with the vehicle outside information feature amount extracted, a face information feature amount for the estimation of the cognitive function of the driver on a basis of the face information acquired;
extracting, in accordance with the vehicle outside information feature amount extracted, a extracting, in accordance with the vehicle outside information feature amount extracted, a biological information feature amount for the estimation of the cognitive function of the driver on a basis of the biological information acquired;
extracting, in accordance with the vehicle outside information feature amount extracted, a extracting, in accordance with the vehicle outside information feature amount extracted, a vehicle information feature amount for the estimation of the cognitive function of the driver on a basis of the vehicle information acquired; and
estimating whether or not the cognitive function of the driver is low on a basis of a machine learning model, the vehicle outside information feature amount extracted, and at least one of the face information feature amount extracted, the biological information feature amount extracted, or the vehicle information feature amount extracted,
wherein, in response to extracting a first vehicle outside information feature amount, the processing circuitry extracts the face information feature amount without extracting the biological information feature amount, and
wherein, in response to extracting a second vehicle outside information feature amount, the processing circuitry extracts both of the face information feature amount and the biological information feature amount.

* * * * *